United States Patent [19]

Leonard

[11] 4,353,799
[45] Oct. 12, 1982

[54] HYDROPHOBIC DIFFUSION MEMBRANES FOR BLOOD HAVING WETTABLE SURFACES

[75] Inventor: Ronald J. Leonard, Harvard, Ill.

[73] Assignee: Baxter Travenol Laboratories, Inc., Deerfield, Ill.

[21] Appl. No.: 901,945

[22] Filed: May 1, 1978

Related U.S. Application Data

[63] Continuation of Ser. No. 687,590, May 19, 1976, abandoned.

[51] Int. Cl.³ ............................................... B01D 31/00
[52] U.S. Cl. ................................... 210/321.3; 264/22; 422/48
[58] Field of Search ................. 210/321 B, 22, 500 M, 210/321.3, 927; 55/16; 427/40; 23/258.5 M; 264/22; 422/48

[56] References Cited

U.S. PATENT DOCUMENTS 3,757,955 9/1973 Leonard .......................... 210/321 B
3,992,495 11/1976 Sano et al. ............................ 264/22

Primary Examiner—Frank A. Spear, Jr.
Attorney, Agent, or Firm—Paul C. Flattery; Thomas R. Schuman; Garrettson Ellis

[57] ABSTRACT

Hydrophobic diffusion membranes such as porous polypropylene may be rendered hydrophilic at their surfaces, without losing their valuable characteristics as diffusion membranes, by subjection to a corona discharge or other ionizing condition, preferably in air or a similar oxygen-containing atmosphere.

31 Claims, 1 Drawing Figure

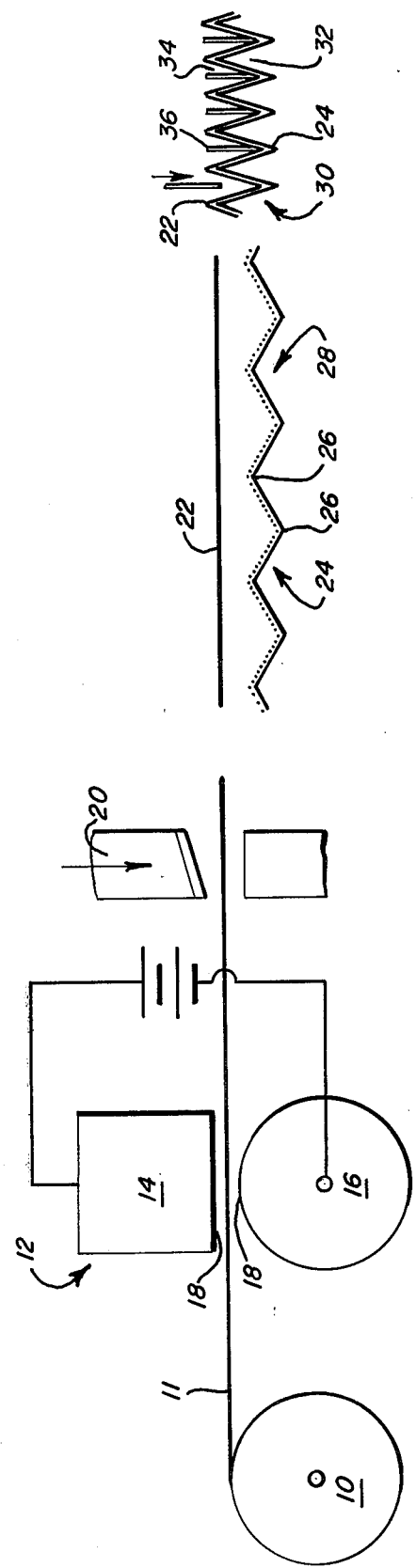

HYDROPHOBIC DIFFUSION MEMBRANES FOR BLOOD HAVING WETTABLE SURFACES

CROSS-REFERENCE TO RELATED APPLICATION

This application is a continuation of application Ser. No. 687,590, filed May 19, 1976, now abandoned.

BACKGROUND OF THE INVENTION

Membrane oxygenators for blood are presently being sold by Travenol Laboratories, Inc., Deerfield, Ill., which contain a microporous, hydrophobic diffusion membrane. The diffusion membrane is pressed between membrane support members, and provided with a pair of flow paths, one for blood along one side of the membrane and another for oxygen and respired gases along the other side of the membrane.

The pores in the hydrophobic material are sufficiently small, compared with the thickness of the material, that blood cannot pass through the membrane. However, the pores provide improved permeability for gases through the membrane. Accordingly, oxygen, carbon dioxide, and water vapor are rapidly exchanged through the membrane. See U.S. Pat. Nos. 3,757,955 and 3,927,980 for descriptions of the construction and use of oxygenators having hydrophobic membranes.

Such oxygenators for blood made of porous, hydrophobic membrane have turned out to be a major step forward in the field of blood oxygenation, and are being used in open heart surgery and other medical procedures with significantly improved success over that which has gone before in the prior art. The devices of this invention exhibit excellent blood compatibility, permitting relatively long-term use, coupled with a high level of blood oxygenation.

However, it has been considered desirable by some experts to use hydrophilic, blood-contacting membranes rather than hydrophobic membranes, for the reason that there is increased compatibility between hydrophilic membranes and the formed elements of the blood, as well as plasma portions, when compared with hydrophobic membranes.

However, hydrophilic membranes may not be rendered porous without causing leakage of aqueous liquids across the membrane, and hydrophilic membranes generally exhibit far less capacity for oxygen and carbon dioxide transfer.

In accordance with this invention, a hydrophobic membrane, preferably a porous, hydrophobic membrane, is provided with a hydrophilic outer surface. Accordingly, the resulting membrane can exhibit the desirable transfer characteristics of hydrophobic membranes, specifically the porous membranes, while at the same time presenting a hydrophilic surface to the blood, resulting in less platelet attachment and the like.

Also, the membranes of this invention, and especially the porous membranes, can be used to process other aqueous liquids in the medical as well as other fields, as well as nonaqueous liquids having surface tensions similar to water, without leakage.

DESCRIPTION OF THE INVENTION

A diffusion device, typically for blood, may be assembled by overlaying membrane support means with a diffusion membrane comprising hydrophobic material, to form a diffusion device defining a first flow path for one fluid along one side of the diffusion membrane, and a second flow path for another fluid along the other side of said diffusion membrane. In accordance with this invention, prior to the overlaying of the support means by the membrane, one surface, typically the blood-contacting surface, of the diffusion membrane is subjected to ionizing atmosphere conditions, so as to increase the surface tension of the membrane surface to render it more hydrophilic.

Typically, the ionizing conditions utilized herein are created by subjecting the membrane to a corona discharge in air. Corona discharge treatment of polyethylene film for other purposes is a well-known and conventional process. Apparatus for subjecting films to a corona discharge is sold by the Pillar Corporation, 7000 West Walker Street, Milwaukee, Wis.

While the specific corona discharge conditions may vary in accordance with the nature of the diffusion membrane to be treated and other conditions, successful results have been obtained with a Pillar Solid State Corona Treater by generating a corona discharge field with 2,000 volt, 4 Kilohertz alternating current, and passing the membrane material through the field. Porous, hydrophobic membranes having a pore size of no more than 5 microns, made of aliphatic hydrocarbons, are generally preferred. Conveniently, both sides of the membrane may be rendered hydrophilic, if desired.

A specific membrane material subjected to the corona discharge field may be a polypropylene membrane having a thickness of 0.001 inch, and an effective pore size of 0.1 micron (Cellgard 2400, manufactured by the Celanese Corporation). By this processing technique, the polypropylene material described above, which normally has a surface tension of about 34 dynes/cm. can be changed to a material having a surface tension of about 60 dynes/cm. However, it may only be necessary to treat the surface only to an extent that the surface becomes wettable to the fluid which it will contact, i.e., the surface tension of the membrane may be raised only to just barely greater than that of the fluid, at the temperature and other conditions of the intended use.

Typically, the process of this invention will be performed in the air, since the presence of oxygen appears to facilitate the process. Accordingly, it is generally preferred that the process be performed in essentially ambient pressures, and in an atmosphere having at least 10 percent oxygen. However, some increase in the surface tension is noted when the diffusion membrane is subjected to corona discharge in, for example, a pure nitrogen atmosphere.

While it is generally preferred to utilize diffusion membranes made of aliphatic hydrocarbon polymers, such as polyethylene and polypropylene, it is contemplated that other membranes may also be altered in their surface tension, such as silicone rubber film and polytetrafluoroethylene films. Also, copolymers of hydrocarbons such as ethylene and propylene, copolymerized with other units such as styrene (for stiffening the membranes), butadiene, and the like may be utilized if desired.

The corona treatment process can be performed on a continuous basis, where each portion of the membrane is exposed to the corona field for only a fraction of a second, if desired, in accordance with the recommendation of the manufacturer of the particular corona discharge unit utilized. It is generally thought that for any particular membrane it may be possible to overtreat the membrane, so that the inner surfaces of the pores of the membrane are also rendered hydrophilic, resulting in an increased capability of the porous membranes to permit fluids from blood and the like to pass through the membrane. This is usually undesirable, and may be avoided by simply reducing the length of exposure of the membrane to the corona discharge field, or the intensity of the field.

It is generally preferable to treat membranes in accordance with this invention to cause their surface tension to increase to at least 50 dynes/cm., to obtain a significant increase in the hydrophilic characteristics of the membrane.

It is also contemplated that other ionizing conditions may be used as well as corona discharge; for example oxygen ions and other ions may be generated by an electric arc in the vicinity of the membrane to be treated, or the membrane may be exposed to various forms of ionizing radiation.

The drawing illustrates a schematic diagram of a method in accordance with this invention for the manufacture of oxygenators for blood.

Referring to the drawing, a roll 10 of porous, hydrophobic membrane 11 is provided, for example the porous polypropylene material described above. The roll of membrane material is unrolled to pass through a corona discharge device 12, which comprises a pair of electrodes 14, 16 with their facing surfaces being covered with an insulating material such as silicone resin or rubber, to create the corona field.

The air in the space between electrodes 14, 16 ionizes during operation. A transformation of the surface of membrane 11 takes place, causing the normal surface tension for the polypropylene material used of about 35 dynes/cm. to increase to about 60 dynes/cm., imparting hydrophilic characteristics to the membrane surface.

Thereafter, the treated membrane passes to a cutting station 20, in which the membrane strip is cut into desired lengths of membrane 22. The lengths of membrane 22 are then laid over and against a membrane support sheet 24, which has been prescored and prefolded along fold lines 26 to form a plurality of sections 28. The specific details of the exact structure of the device being made may be as described in U.S. Pat. No. 3,757,955.

Thereafter, membrane 22 and membrane support 24 may be folded together into a convoluted, pleated structure 30 to form a diffusion stack defining a series of flow channels 32 on one side of the stack for the passage of oxygen gas, and another series of flow channels 34 on the other side of membrane 22 for the passage of blood, as described in the U.S. patent mentioned above. Additional membrane support structures 36 may be added to the blood flow paths as desired.

The entire stack 30 is then inserted in a suitable container, having manifold ports for the inlet and outlet of gas and blood. The container is sealed, and the device is sterilized in suitable manner for use.

While the method of this invention finds particular utility in diffusion devices for blood, it is also contemplated that other types of diffusion devices may also be made in accordance with this invention.

The above has been offered for illustrative purposes only, and is not for the purpose of limiting the invention of this application, which is as defined in the claims below.

That which is claimed is:

1. In the method of assembling a diffusion device which comprises overlaying membrane support means with a diffusion membrane comprising hydrophobic material and further defining a large number of pores having effective diameters of no more than five microns, to form a diffusion device defining a first flow path for one fluid along one side of said diffusion membrane, and a second flow path for another fluid along the other side of said diffusion membrane, the improvement comprising:

prior to said overlaying step, subjecting the outer surface of said diffusion membrane to ionizing atmosphere conditions, whereby the surface tension of said outer surface of the membrane is increased over the surface tension of the internal portions of said membrane defining said pores.

2. The method of claim 1 in which said ionizing conditions are created by subjecting said membrane to a corona discharge field.

3. The method of claim 2 in which said corona discharge field is in an atmosphere of at least 10 percent by weight of oxygen.

4. The method of claim 3 in which said diffusion membrane defines a large number of pores having effective diameters of at least 0.1 micron.

5. The method of claim 4 in which said diffusion membrane is made of an aliphatic hydrocarbon polymer.

6. The method of claim 5 which further comprises controlling the extent of said ionizing atmosphere conditions whereby the inner surfaces of the pores of said diffusion membrane do not exhibit significantly increased surface tension over the normal surface tension of said hydrophobic material, while the exterior surfaces of said membrane exhibit increased surface tension.

7. The method of claim 5 in which said aliphatic hydrocarbon polymer is polypropylene.

8. The method of claim 7 in which said corona discharge is created with 2,000 volt, 4 Kilohertz alternating current.

9. The method of claim 1 in which said diffusion membrane retains, after said exposure to ionizing atmosphere conditions, a surface tension within said pores which is less than the surface tension of the outer surface of said membrane.

10. In a diffusion device for blood which comprises membrane support means overlaid with a diffusion membrane comprising hydrophobic material, said diffusion device defining a first flow path for one fluid along one side of the diffusion membrane, and a second flow path for another fluid along the other side of the diffusion membrane, the improvement comprising: said hydrophobic diffusion membrane defining a large number of pores of no more than five microns in diameter, and a corona discharge-created, hydrophilic outer surface exhibiting a surface tension of at least 50 dynes/cm., whereby said membrane exhibits less platelet attachment in contact with blood, when compared with a corresponding, hydrophobic diffusion membrane which has not been treated with a corona discharge.

11. The apparatus of claim 10 in which said diffusion member defines a large number of pores of at least 0.1 micron in effective diameter.

12. The diffusion device of claim 11 in which the average effective pore size of said diffusion membrane is no more than 1 micron.

13. The apparatus of claim 12 in which said diffusion membrane comprises an aliphatic hydrocarbon polymer.

14. The diffusion device of claim 13 in which said membrane comprises polypropylene.

15. The diffusion device of claim 10 in which said diffusion membrane retains, after said exposure to ionizing atmosphere conditions, a surface tension within said pores which is less than the surface tension of the outer surface of said membrane.

16. In the method of rendering hydrophobic, porous diffusion membrane more compatable to blood, the improvement comprising subjecting said diffusion membrane to ionizing atmosphere conditions, whereby the surface tension of said membrane surface, but not the interiors of the pores, is increased to render it hydrophilic.

17. The method of claim 16 in which said ionizing atmosphere conditions are created by subjecting said membrane to corona discharge.

18. The method of claim 17 in which said corona discharge is performed in an atmosphere of at least 10 percent by weight of oxygen.

19. The method of claim 18 in which the average pore size of said membrane is no more than 1 micron.

20. The method of claim 19 in which said membrane comprises an aliphatic hydrocarbon polymer.

21. The method of claim 20 in which said membrane comprises polypropylene.

22. The method of claim 21 in which the corona discharge raises the surface tension of said membrane to at least 50 dynes/cm.

23. The method of claim 22 in which said corona discharge is created with 2000 volt, 4 Kilohertz alternating current.

24. The method of claim 16 which further comprises controlling the extent of said ionizing atmosphere conditions whereby the inner surfaces of the pores of said diffusion membrane do not exhibit significantly increased surface tension over the normal surface tension of said hydrophobic diffusion membrane, while the exterior surfaces of said membrane exhibit said increased surface tension.

25. The method of claim 16 in which said diffusion membrane retains, after said exposure to ionizing atmosphere conditions, a surface tension within said pores which is less than the surface tension of the outer surface of said membrane.

26. In a diffusion device which comprises membrane support means overlaid with a hydrophobic diffusion membrane, said diffusion device defining a first flow path for one fluid along one side of the diffusion membrane, and a second flow path for another fluid along the other side of the diffusion membrane, the improvement comprising:

said hydrophobic diffusion membrane being porous and defining a corona discharge-created surface, exhibiting a more hydrophilic, higher surface tension than the surface tension of said hydrophilic material within said pores, said corona discharge created surface being in contact with said second flow path, said second flow path being adapted for conveying liquid to be treated by the diffusion device.

27. The diffusion device of claim 26 in which said diffusion membrane retains, after said exposure to ionizing atmosphere conditions, a surface tension within said pores which is less than the surface tension of the outer surface of said membrane.

28. A method of providing to hydrophobic, porous diffusion membrane, an outer surface having a surface tension which is increased over the surface tension of said hydrophobic membrane within said pores, which comprises: subjecting said hydrophobic, porous diffusion membrane to ionizing atmosphere conditions.

29. The method of claim 28 in which said ionizing atmosphere conditions comprise a corona discharge in an atmosphere containing at least ten percent by weight of oxygen.

30. The method of claim 29 which further comprises controlling the extent of said ionizing atmosphere conditions whereby the inner surfaces of the pores of said diffusion membrane do not exhibit significantly increased surface tension over the normal surface tension of said hydrophobic membrane, while the exterior surfaces of said membrane exhibit said increased surface tension.

31. A hydrophobic, porous diffusion membrane, said pores having effective diameters of essentially 0.1 to 5 microns, defining a surface tension at its outer surface which is increased over the normal surface tension of said hydrophobic membrane, the surface tension of the interiors of said pores being less than said increased surface tension.

* * * * *